Figure 1:
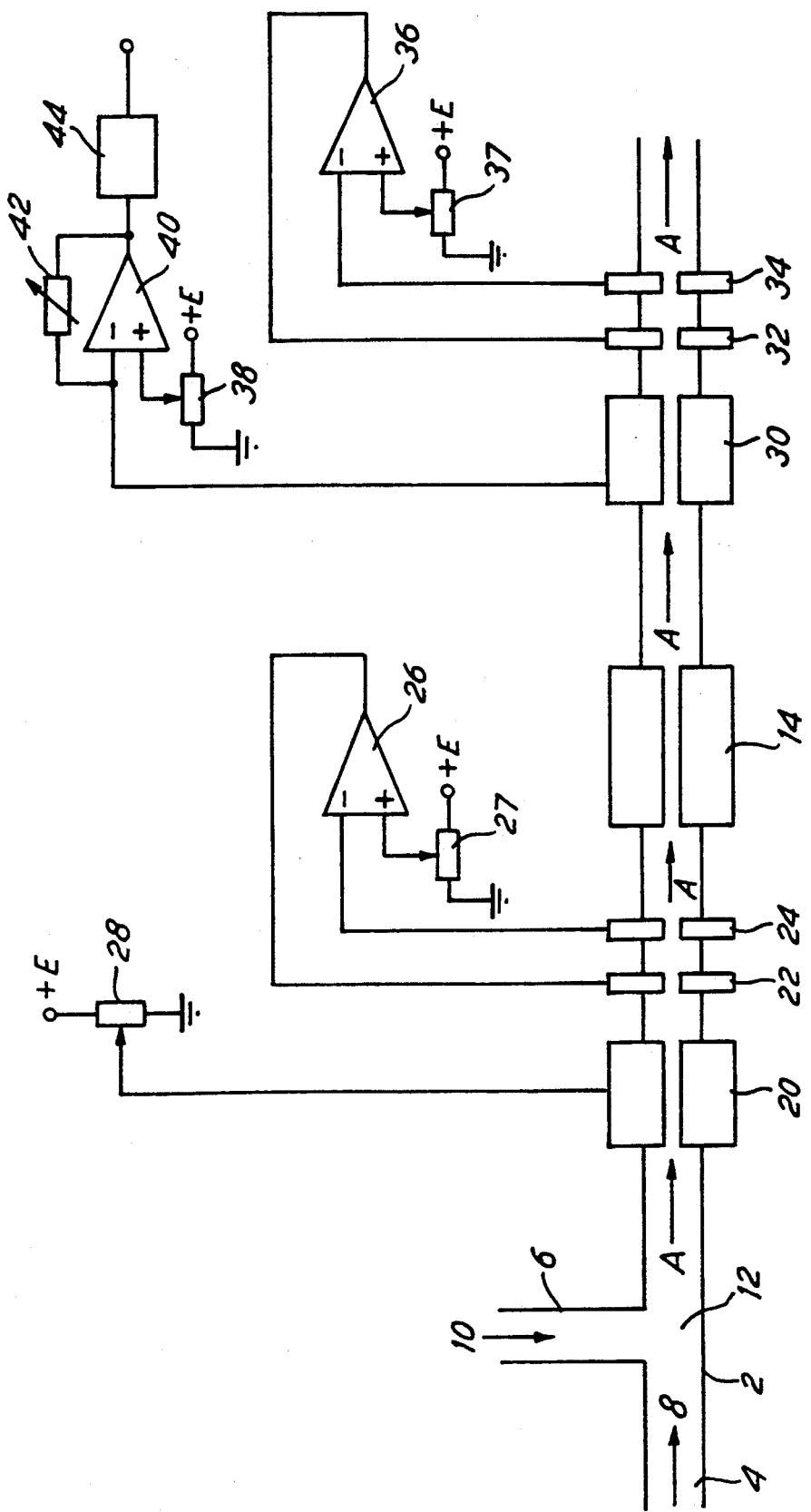

United States Patent [19]

Cattell

[11] Patent Number: 5,206,145
[45] Date of Patent: Apr. 27, 1993

[54] METHOD OF MEASURING THE CONCENTRATION OF A SUBSTANCE IN A SAMPLE SOLUTION

[75] Inventor: Alan F. Cattell, Buckinghamshire, England

[73] Assignee: Thorn EMI plc, London, England

[21] Appl. No.: 751,670

[22] Filed: Aug. 23, 1991

Related U.S. Application Data

[63] Continuation of Ser. No. 354,038, May 19, 1989, abandoned.

[30] Foreign Application Priority Data

May 19, 1988 [GB] United Kingdom ............... 8811860

[51] Int. Cl.$^5$ .................. G02N 27/26; C12Q 1/26; C12Q 1/54
[52] U.S. Cl. .................. 435/14; 435/25; 435/817; 204/153.12; 204/403
[58] Field of Search .............. 435/14, 25, 288, 291, 435/817; 204/403, 153.12, 412

[56] References Cited

U.S. PATENT DOCUMENTS

| | | | |
|---|---|---|---|
| 3,367,849 | 2/1968 | Blaedel et al. | 422/81 |
| 3,707,455 | 12/1972 | Derr et al. | 204/415 |
| 3,813,325 | 5/1974 | Merrell et al. | 204/403 |
| 3,902,970 | 9/1975 | Levin . | |
| 3,919,051 | 11/1975 | Koch et al. | 435/14 |
| 4,105,522 | 8/1978 | Friedenberg et al. | 204/406 |
| 4,153,513 | 5/1979 | Edelmann et al. | 435/288 |
| 4,224,125 | 9/1980 | Nakamura et al. | 204/195 B |
| 4,244,787 | 1/1981 | Klein et al. | 204/403 |
| 4,260,680 | 4/1981 | Muramatsu et al. | 204/153.12 |
| 4,490,235 | 12/1984 | Calzi | 204/153.12 |
| 4,655,880 | 4/1987 | Liu | 204/153.12 |
| 4,758,323 | 7/1988 | Davis et al. | 204/403 |
| 4,830,959 | 5/1989 | McNeil et al. | 435/7 |
| 5,037,737 | 8/1991 | Liffman et al. | 204/153.12 |

FOREIGN PATENT DOCUMENTS

| | | | |
|---|---|---|---|
| 0102458 | 3/1984 | European Pat. Off. . | |
| 0122009 | 10/1984 | European Pat. Off. . | |
| 0299660 | 1/1989 | European Pat. Off. | 435/288 |
| 0371490 | 6/1990 | European Pat. Off. | 435/288 |
| 0407992 | 1/1991 | European Pat. Off. | 435/288 |
| 2643150 | 8/1990 | France | 435/288 |
| 0216947 | 12/1983 | Japan . | |
| 1516338 | 7/1978 | United Kingdom . | |
| 2002127 | 2/1979 | United Kingdom | 435/288 |
| 2063479 | 6/1981 | United Kingdom . | |

*Primary Examiner*—Robert J. Warden
*Assistant Examiner*—T. A. Trembley
*Attorney, Agent, or Firm*—Keck, Mahin & Cate

[57] ABSTRACT

An apparatus is provided for measuring the concentration of a substance in a sample solution. The apparatus comprises first electrode means, second electrode means and an enzyme channel between the first and second electrode means. The enzyme channel contains an enzyme for catalysing a reaction of the substance whose concentration is to be measured. In use, a known volume of the sample solution is presented to the first electrode means in a test solution including an excess of a mediator, one of reduction or oxidation of the mediator being coupled to the reaction of the substance. The first electrode means is arranged to ensure that the mediator is respectively completely oxidized or reduced, and also to remove any interferent species. The test solution is then passed through the enzyme channel so as to permit reaction of all of the substance present in the solution, whereby a quantity of the mediator is respectively reduced or oxidized. The test solution is then presented to the second electrode means which are arranged to respectively oxidize or reduce the quantity of mediator which had been respectively reduced or oxidized. This produces a quantity of charge through the second electrode means which is measured by means for measuring said quantity of charge.

6 Claims, 1 Drawing Sheet

METHOD OF MEASURING THE CONCENTRATION OF A SUBSTANCE IN A SAMPLE SOLUTION

This application is a continuation of application Ser. No. 07/354,038, filed May 19, 1989, now abandoned.

This invention relates to a method of and an apparatus for measuring the concentration of a substance, such as a metabolite, in a solution. In particular it relates to a method of and an apparatus for measuring the concentration of a metabolite in a flowing solution by means of an enzymatic reaction.

One frequently measured metabolite is glucose. A method of monitoring the concentration of glucose in a flowing solution is disclosed in U.S. Pat. No. 3,902,970 (Levin). A sample of a solution to be tested is passed through a column comprising the enzyme glucose oxidase immobilized on glass beads, where the glucose is converted to gluconic acid and hydrogen peroxide. The concentration of hydrogen peroxide is measured in a small-bore flow-through amperometric cell having measuring, counter and reference electrodes. The current flowing from the measuring electrode when a constant potential is applied between the measuring and reference electrodes gives a measure of the hydrogen peroxide concentration and hence of the glucose concentration in the test solution. The method, however, has a number of disadvantages. Firstly, the measuring electrode will also oxidize other species present in the solution. Secondly, the glucose oxidase presently available inevitably contains the enzyme catalase which consumes hydrogen peroxide. Thirdly the reaction rate is dependent on the oxygen concentration in the solution and not even oxygen saturated blood contains enough oxygen to complete the reaction. All these contribute to errors in the measurement of the concentration of glucose in the sample.

Another method of monitoring the concentration of glucose in a flowing solution is disclosed in U.S. Pat. No. 3,367,849 (Blaedel et al). The test solution is mixed with a buffer solution containing ferrocyanide and glucose oxidase to form electro-reducible ferricyanide at a rate proportional to the amount of glucose present in the test solution. The mixed solution passes through a first small-bore tubular electrode, through an interelectrode solution delay section, to allow time for ferricyanide to be formed, and through a second small-bore tubular electrode. The first and second electrodes form two arms of a bridge. A bridge circuit senses the change in potential between the two halves of the bridge corresponding to a difference in the currents through the first and second electrodes due to the ferricyanide formed in the interelectrode solution delay line. However, the measurement of the concentration of glucose in the sample, as disclosed, relies on the assumption that the catalyzed reaction of the glucose proceeds, during a certain stage of the reaction, at a linear rate dependent on the concentration of glucose—a delay line having to be provided in the apparatus to allow the oxidation of glucose to be initiated so as to proceed at the linear rate. Accordingly, such an apparatus which relies on the measurement of a reaction rate at a certain stage in the reaction produces problems which are not present in an apparatus which measures the quantity of a substance per se.

It is an object of the present invention to provide a method and an apparatus for measuring the concentration of a substance in a solution which at least alleviates some of the problems outlined hereinbefore.

According to a first aspect of the present invention there is provided a method of measuring the concentration of a substance in a sample solution using an enzyme for catalyzing a reaction of a said substance, the method comprising the steps of:

a) preparing a test solution comprising a known volume of a said sample solution and an excess of a mediator, one of reduction or oxidation of the mediator being coupled to a said reaction;

b) presenting the test solution to first electrode means arranged to ensure that the mediator is respectively completely oxidized or reduced, and to remove any interferent species;

c) passing the test solution through an enzyme channel containing a said enzyme so as to permit reaction of all of said substance present in the test solution, whereby a quantity of the mediator is respectively reduced or oxidized;

d) then presenting the test solution to second electrode means arranged to respectively oxidized or reduce said quantity of the mediator whereby a quantity of charge is produced through said second electrodes;

e) measuring said quantity of charge.

In a method provided in accordance with the invention, because the mediator in the test solution is respectively fully oxidized or reduced before the test solution is passed through the enzyme channel, all of the mediator respectively reduced or oxidized in the solution presented to said second electrode means has been respectively reduced or oxidized by coupling to said reaction of said substance in the enzyme channel. Accordingly, as any interferent species present in the test solution have been removed, the quantity of charge produced and measured at said second electrode means due to subsequent respective oxidation or reduction of the mediator is a direct measure of the quantity of said substance in the test solution and hence the concentration of said substance in the sample solution. The method thus provides an absolute measurement of the concentration of said substance in the sample solution without the need for pre-calibration of the apparatus used.

According to a second aspect of the present invention, there is provided an apparatus for measuring the concentration of a substance in a sample solution, the apparatus comprising first electrode means, second electrode means and an enzyme channel between said first and said second electrode means, the enzyme channel containing an enzyme for catalyzing a reaction of a said substance; wherein, in use, a known volume of a said sample solution is presented to said first electrode means in a test solution including an excess of a mediator, one of reduction or oxidation of the mediator being coupled to a said reaction of a said substance, said first electrode means being arranged to ensure that the mediator is respectively completely oxidized or reduced, and to remove any interferent species; the test solution then being passed through the enzyme channel so as to permit reaction of all of said substance present in a said solution, whereby a quantity of the mediator is respectively reduced or oxidized; the test solution then being presented to said second electrode means arranged to respectively oxidize or reduce said quantity of the mediator producing a quantity of charge through said second electrode means; the measuring system further comprising means for measuring said quantity of charge.

Such an apparatus which measures the concentration of a substance in a sample solution in accordance with the method of the present invention provides an absolute measurement of that concentration without the need for precalibration.

Preferably the apparatus further comprises means for producing the test solution from a known volume of the sample solution and a solution of the mediator in an appropriate buffer. The first and second electrode means may accordingly be conditioned by the mediator solution, before the sample solution is added, until the current passed falls essentially to zero. This reduces or overcomes the start-up problem commonly observed with such electrode means.

When the substance whose concentration is to be measured is glucose, preferably the enzyme used is glucose oxidase which oxidizes glucose. A suitable mediator is ferrocyanide for which a suitable buffer includes a phosphate.

An embodiment of the invention will now be described, by way of example only, with reference to the accompanying FIG. 1 which shows an apparatus for measuring the concentration of a substance in a sample in accordance with the invention.

Referring to FIG. 1, an apparatus for measuring the concentration of a substance in a sample solution comprises a tube 2 having a first inlet 4 and a second inlet 6. In use, a solution 8 containing a suitable buffer (e.g. a phosphate buffer) and a mediator, the amount of mediator being at least ten times greater than that required for the concentration measurement, flows into the apparatus through the first inlet 4. A suitable mediator is ferrocyanide $[Fe(CN)_6]^{4-}$ for which the oxidized state is ferricyanide $[Fe(CN)_6]^{3-}$. A blood sample 10 of known volume is fed into the flowing solution 8 via the second inlet 6 producing a test solution at the junction 12 of the first and second inlets 4, 6.

The direction of flow of the test solution 12 is indicated in the Figure by the arrows A. The test solution 12 flows through a first set of electrodes comprising a first working electrode 20, a reference electrode 22 and a counter electrode 24; through an enzyme column 14 and then through a second set of electrodes comprising a second working electrode 30, a reference electrode 32 and a counter electrode 34 and then out to waste or storage.

There are similarities in the electrical circuitry associated with the first electrode means 20, 22, 24 and with the second electrode means 30, 32, 34. A differential amplifier 26, 36 automatically adjusts the current between the working electrode 20, 30 and counter electrode 24, 34 to maintain a constant potential difference between the working electrode 20, 30 and the reference electrode 22, 32 in known manner. The inverting input of the amplifier 26, 36 is connected to the counter electrode 24, 34 and the output of the amplifier 26, 36 to the reference electrode 22, 32. The potential difference between the working electrode 20, 30 and the reference electrode 22, 32 is determined by a potentiometer 27, 37 connected to the non-inverting input of the amplifer 26, 36 and by a potentiometer 28, 38 coupled to the working electrode 20, 30. The circuit coupled to the second working electrode 30 also comprises a differential amplifier 40, having the potentiometer 38 connected to its non-inverting input and a variable resistor 42 connected between its inverting input and its output. A current integrator 44 connected to the output of the amplifier 40 digitizes and integrates current flowing from the working electrode 30 to give an output which corresponds to the quantity of charge flowing from the electrode 30.

The first electrode means 20, 22, 24 ensures that the mediator in the test solution is completely oxidized and that species including ions which might interfere with the measurement (i.e. interferent species), such as ascorbic acid, are removed from the solution. The enzyme column 14 comprises a porous column whose surfaces contain the enzyme glucose oxidase, providing an enzyme channel. The enzyme catalyzes the reaction of the glucose present in the blood sample to form gluconic acid. This reaction is coupled to reduction of the mediator, two ions of reduced ferrocyanide being produced for each molecule of glucose in the solution. The reduced mediator is then re-oxidizes at the second electrode means 30, 32, 34 by the working electrode 30, to produce a current.

It is envisaged that other first and second electrode means may be provided. The first electrode means ensures that the mediator is completely oxidized and that any interferent species are removed. The second electrode means re-oxidises the mediator reduced in the enzyme channel.

As aforementioned, the current flowing from the electrode 30 is integrated to give an output corresponding to the quantity of charge flowing from the electrode 30. The quantity of charge provides a measure of the quantity of mediator re-oxidised by the electrode 30 and hence of the amount of glucose present in the test solution. The number of electrons used to re-oxidize the mediator is $Q/e$, where Q is the total charge provided, as measured by the current integrator 10, and e is the charge on an electron. Thus the number of glucose molecules in the blood sample of volume V is given by $Q/2e$ and the concentration of the glucose in the blood sample is $Q/2eV$ molecules per unit volume.

The critical requirements for the apparatus provided in accordance with the invention to measure the concentration of glucose using the enzyme glucose oxidase are as follows:

1. The volume V of the sample solution used is accurately known.

2. The mediator is completely oxidized at both the first and second electrode means. This depends on the electrode area and on the solution flow rate, as outlined below.

The measurement is not diffusion limited provided that the diffusion time for the reduced mediator to diffuse from the bulk solution above the electrodes to the electrode surface is much shorter than the time for the solution to flow the length of the electrode. With a 2:1 dilution factor of the blood sample in the flowing solution, and with electrodes of area 1 $cm^2$, it should be possible to perform such a measurement in well under one minute using 50 $\mu$l of solution.

3. All the glucose present is catalyzed by the enzyme to form gluconic acid. This depends on the solution flow rate, i.e. the time during which the test solution is in the enzyme channel should be greater than the time for the reaction of the glucose present in the solution to take place.

The buffer solution 8 can be used to stabilize the first and second electrode means before a sample solution is added and to cleanse the apparatus between measurements of successive test samples.

The method and apparatus described hereinbefore is with reference to the measurement of glucose concentration in a blood sample. A method and apparatus may be provided in accordance with the invention for similar measurements to determine the concentration of any metabolite (or other substance) for which there is a reaction which can be catalyzed by an enzyme and which can be coupled to the oxidation or reduction of a mediator.

I claim:

1. A method for the absolute measurement of the concentration of a substance in a predetermined volume of a sample solution comprising;
    (a) providing an apparatus comprising first and second electrode structures and an enzyme channel between said first and second electrode structures containing an enzyme for catalyzing a reaction of a substance contained in a predetermined volume of a sample solution;
    (b) providing a mixture of an excess of a mediator and said sample solution, presenting said mixture to the first electrode structure and applying a voltage to said first electrode structure effective to oxidize said mediator and electrochemically remove any interferent species present in said sample solution;
    (c) passing the mixture through the enzyme channel effective to catalyze a reaction of all of said sample substance such that a quantity of said mediator is reduced;
    (d) presenting the mixture to the second electrode structure and applying a voltage to said second electrode structure effective to completely re-oxidize all of said quantity of reduced mediator;
    (e) measuring the current flowing through said second electrode structure required to completely re-oxidize all of said quantity of reduced mediator;
    (f) integrating said current to provide a measurement of the quantity of charge required to completely re-oxidize all of said quantity of reduced mediator, and,
    calculating the concentration of the sample substance in said sample solution from said measurement.

2. A method according to claim 1 further comprising providing a buffer solution and presenting the buffer solution to the first and second electrode structures prior to presenting said mixture to the first electrode structure.

3. A method according to claim 1 wherein the substance is glucose and the enzyme is glucose oxidase.

4. A method for the absolute measurement of the concentration of a substance in a predetermined volume of a sample solution comprising;
    (a) providing an apparatus comprising first and second electrode structures and an enzyme channel between said first and second electrode structures containing an enzyme for catalyzing a reaction of a substance contained in a predetermined volume of a sample solution;
    (b) providing a mixture of an excess of a mediator and said sample solution, presenting said mixture to the first electrode structure and applying a voltage to said first electrode structure effective to reduce said mediator and electrochemically remove any interferent species present in said sample solution;
    (c) passing the mixture through the enzyme channel effective to catalyze a reaction of all of said sample substance such that a quantity of said mediator is oxidized;
    (d) presenting the mixture to the second electrode structure and applying a voltage to said second electrode structure effective to completely re-reduce all of said quantity of oxidized mediator;
    (e) measuring the current flowing through said second electrode structure required to completely re-reduce all of said quantity of oxidized mediator;
    (f) integrating said current to provide a measurement of the quantity of charge required to completely re-reduce all of said quantity of oxidized mediator, and,
    calculating the concentration of the sample substance in said sample solution from said measurement.

5. A method according to claim 4 further comprising providing a buffer solution and presenting the buffer solution to the first and second electrode structures prior to presenting said mixture to the first electrode structure.

6. A method according to claim 4 wherein the substance is glucose and the enzyme is glucose oxidase.

* * * * *